(12) United States Patent
Wilson (10) Patent No.: US 9,695,389 B2
(45) Date of Patent: *Jul. 4, 2017

(54) BIOREACTOR USING A MACROALGAE

(71) Applicant: Tristan Victor Wilson, Danby, VT (US)

(72) Inventor: Tristan Victor Wilson, Danby, VT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/179,515

(22) Filed: Jun. 10, 2016

(65) Prior Publication Data

US 2016/0281041 A1 Sep. 29, 2016

Related U.S. Application Data

(63) Continuation of application No. 14/935,018, filed on Nov. 6, 2015, now Pat. No. 9,388,372.

(60) Provisional application No. 62/077,040, filed on Nov. 7, 2014.

(51) Int. Cl.
| | |
|---|---|
| C12M 1/00 | (2006.01) |
| C12M 1/02 | (2006.01) |
| A01K 63/00 | (2017.01) |
| A01K 63/06 | (2006.01) |
| F28D 15/02 | (2006.01) |
| F28D 15/04 | (2006.01) |
| A01G 33/00 | (2006.01) |
| F21V 15/01 | (2006.01) |
| F21V 29/51 | (2015.01) |
| F21V 29/89 | (2015.01) |
| F21Y 101/00 | (2016.01) |
| F21Y 103/00 | (2016.01) |
| F21Y 103/10 | (2016.01) |
| F21Y 101/02 | (2006.01) |

(52) U.S. Cl.
CPC ............ *C12M 21/02* (2013.01); *A01G 33/00* (2013.01); *A01K 63/006* (2013.01); *A01K 63/06* (2013.01); *A01K 63/065* (2013.01); *C12M 23/38* (2013.01); *C12M 31/10* (2013.01); *C12M 41/18* (2013.01); *F21V 15/01* (2013.01); *F21V 29/51* (2015.01); *F21V 29/89* (2015.01); *F28D 15/04* (2013.01); *F21Y 2101/02* (2013.01); *F21Y 2103/00* (2013.01); *F21Y 2103/10* (2016.08); *F28D 15/02* (2013.01)

(58) Field of Classification Search
CPC ...... C12M 21/02; C12M 31/10; C12M 31/08; C12M 41/10; C12M 23/02; C12M 23/56; C12M 27/20; C12M 41/18; C12M 43/04; C12M 23/22; C12M 23/38; C12M 23/58; C12M 33/00; C12M 23/44; C12M 41/06; C12M 41/24; A01G 33/00; A01K 63/006; A01K 63/06; A01K 63/065; F21V 15/01; F21V 29/51; F21V 29/89; F21Y 2101/02; F21Y 2103/00; F21Y 2103/10; F28D 15/02; F28D 15/04

See application file for complete search history.

(56) References Cited

U.S. PATENT DOCUMENTS

| | | |
|---|---|---|
| 2,867,945 A | 1/1959 | Gotaas et al. |
| RE24,822 E | 5/1960 | Pallotta et al. |
| 4,333,263 A | 6/1982 | Adey |
| 4,966,096 A | 10/1990 | Adey |
| 4,995,980 A | 2/1991 | Jaubert |
| 5,097,795 A | 3/1992 | Adey |
| 5,176,100 A | 1/1993 | Fujino |
| 5,326,475 A | 7/1994 | Kent |
| 5,527,456 A | 6/1996 | Jensen |
| 5,536,398 A | 7/1996 | Reinke |
| 5,573,669 A | 11/1996 | Jensen |
| 5,799,612 A | 9/1998 | Page |
| 5,846,423 A | 12/1998 | Jensen |
| 5,863,426 A | 1/1999 | Yen |
| 6,730,226 B2 | 5/2004 | Takada |
| 7,434,964 B1 | 10/2008 | Zheng et al. |
| 7,578,933 B1 | 8/2009 | Selman |
| 7,744,250 B2 | 6/2010 | Lee et al. |
| 7,824,904 B1* | 11/2010 | Dimanshteyn ......... C12M 21/02 362/101 |
| 7,845,814 B2 | 12/2010 | Crabb et al. |
| 8,047,686 B2 | 11/2011 | Dahm et al. |
| 8,100,560 B2 | 1/2012 | Ahland, III et al. |
| 8,470,584 B2 | 6/2013 | Bayles et al. |
| 8,955,249 B2 | 2/2015 | Veres et al. |

(Continued)

FOREIGN PATENT DOCUMENTS

| | | |
|---|---|---|
| WO | 90/01263 A1 | 2/1990 |
| WO | 2011/089077 A1 | 7/2011 |
| WO | 2013/101775 A1 | 7/2013 |
| WO | 2013/138201 A1 | 9/2013 |

OTHER PUBLICATIONS

Dawes, Clinton J. "Macroalgae", Chapter 6 in Marine Botany (2nd edition, 1998); pp. 113-167.

(Continued)

*Primary Examiner* — Debbie K Ware
(74) *Attorney, Agent, or Firm* — Fox Rothschild LLP (57) ABSTRACT

The invention features a bioreactor for the growth of macroalgae and methods for using the bioreactor to maintain optimal nutrient levels for the organisms in an aquarium or aquaculture system. The devices and methods of the invention provide for the bioremediation of excess nutrients in order to maintain nutrient balance in an aquarium or aquaculture system that facilitates growth and/or health of one or more of the organisms that reside therein.

12 Claims, 10 Drawing Sheets

(56) References Cited

U.S. PATENT DOCUMENTS

| | | | | |
|---|---|---|---|---|
| 9,206,388 B1* | 12/2015 | Collins | .................... | C12N 1/12 |
| 2011/0117632 A1* | 5/2011 | Woerlee | ................. | C12M 21/02 |
| | | | | 435/257.1 |
| 2012/0079755 A1 | 4/2012 | Torres et al. | | |
| 2013/0233779 A1 | 9/2013 | Farrish | | |
| 2013/0280757 A1* | 10/2013 | Dvorak | .................. | C12M 21/02 |
| | | | | 435/41 |
| 2014/0073035 A1* | 3/2014 | Friederich | .............. | C12M 21/02 |
| | | | | 435/257.1 |
| 2016/0046899 A1* | 2/2016 | Garnier | .................. | C12M 21/02 |
| | | | | 435/292.1 |
| 2016/0083679 A1* | 3/2016 | Johnson | ................. | C12M 21/02 |
| | | | | 435/292.1 |

OTHER PUBLICATIONS

Xu, Y. et al., "Effect of Temperature, Salinity, and Light Intensity on the Growth of Green Macroaga, Chaetomorpha Linum", J. World Aqua. Soc. (2008); vol. 39:6; pp. 847-851.

Invitation to Pay Additional Fees and, where applicable, protest fee, dated Dec. 18, 2015 issued in counterpart International application No. PCT/US2015/059548.

Response to Invitation dated Dec. 18, 2015 filed Jan. 19, 2016 in counterpart International application No. PCT/US2015/059548.

Notification of Decision on Protest or Declaration that Protest Considered not to have been made dated Feb. 24, 2016 in counterpart International application No. PCT/US2015/059548.

* cited by examiner

BIOREACTOR USING A MACROALGAE

CROSS REFERENCE TO RELATED APPLICATIONS

This application is a continuation of U.S. application Ser. No. 14/935,018, filed Nov. 6, 2015, which claims the benefit of priority to U.S. Application No. 62/077,040 filed Nov. 7, 2014, each of which is incorporated herein by reference in its entirety.

FIELD OF THE INVENTION

The present invention provides devices and methods for the bio-absorption of targeted excess nutrients in order to maintain nutrient balance in an aquarium or aquaculture system that facilitates growth and/or health of one or more of the organisms that reside therein. Specifically, the invention provides a bioreactor for the growth of macroalgae and methods for using the bioreactor to maintain optimal nutrient levels for the organisms in the aquarium or aquaculture system.

BACKGROUND OF THE INVENTION

The maintenance of tropical, sub-tropical, and temperate aquaria requires a delicate balance of macro nutrients including nitrogen (N), phosphorus (P), potassium (K), and carbon (C). Overabundance of nutrients can lead to detrimental pH fluctuations, overgrowth of nuisance organisms, and reduced health and/or growth of organisms in the aquarium. For example phosphate inhibits coral's ability to deposit new skeletal growth. The devices and methods of the present invention function to provide a balance of nutrients in an aquarium or aquaculture system.

The devices of the present invention differ from refugiums in several key ways. Refugiums are external tanks that are connected to the main aquarium tank and serve as a separate location for the growth of plants and/or animals free from predation by, e.g., fish in the main tank. Refugiums can be used to support the growth of macroalgae in attempt to control nutrient levels in the main tank. Refugiums, however, are not considered to be an efficient means of controlling nutrient levels or diurnal pH swings. Due to inefficient water flow and lighting, refugiums are not sufficient to control excess nutrients like phosphate and/or prevent daily swings in pH. Further, refugiums are open to the atmosphere allowing direct incorporation of carbon from the air, which can lead to the synthesis of dissolved organic carbon compounds (e.g., polysaccharides) that yellow the water.

Walter H. Adey (U.S. Pat. Nos. 4,966,096 and 5,097,795) describes a "water purification system" that contains a screen that provides an algal-growing surface placed in a moveable, substantially flat, horizontally-positioned, tray-shaped receptacle. The apparatus described by Adey utilizes microalgae in an open-air system that incorporates mechanisms for exposing the algal turf to simulated tide and waves. These devices incorporate complicated mechanisms to simulate surf. For example, in an embodiment described by Adey, the tray, on which the algal turf attaches, accumulates water from the aquarium tank until the weight of the water causes the tray to tilt, dumping the water and allowing the tray to return to its original horizontal position.

Kyle R. Jensen (U.S. Pat. Nos. 5,527,456; 5,573,669 and 5,846,423) describes a method for purifying water that comprises a flat waterway with a screen or similar substrate at the bottom as a microalgae growing surface. Jensen, like Adey utilizes an open-air system with periodic surges of water over the surface of the algal turf The present invention offers several advantages over the prior art. The present invention provides an optimal exposure to light to facilitate growth of the macroalgae, which is utilized as part of the invention. The present invention also provides ease of maintenance and the ability to control the levels of one or more nutrients in the main tank via bioadsorption by the macroalgae and nutrient supplementation. In one embodiment, the bioreactor of the present invention provides a closed loop system that is not directly exposed to the atmosphere, limiting the contained macroalgae to carbon from the main tank. In addition, the present invention avoids the complicated mechanisms described by Jensen and Adey.

SUMMARY OF THE INVENTION

The present invention features a bioreactor for the bio-absorption of targeted nutrients in an aquarium or aquaculture system comprising a light assembly that is mounted in an armature assembly comprising a light-transmissible tube and support structures for the growth of macroalgae, wherein the armature assembly is mounted within an outer chamber assembly, and wherein the light transmissible tube and the outer chamber define a growth chamber for the macroalgae. In one embodiment, the light assembly is removably mounted in the armature assembly. In one embodiment, the growth chamber is substantially sealed from the surrounding atmosphere when the bioreactor is in use.

In one embodiment, the light assembly comprises a light source and a cooling system. In one embodiment, the light source has a coaxial orientation with respect to the growth chamber. In one embodiment, the light assembly comprises a light source selected from the group consisting of a LED, a fluorescent light, a light emitting cathode (LEC), and side emitting fiber optics. In one embodiment the light source comprises a plurality of LED lights, for example, one or more LED arrays. In one embodiment, the light source comprises one or more LED flexible arrays. In one embodiment, the plurality of LED lights comprises two or more types of LEDs that each emit light at different wavelengths. For example, in one embodiment, the plurality of LED lights comprises LEDs that emit predominately at about 450 nm wavelength light and LEDs that emit at about 650 nm wavelength light.

In one embodiment, the cooling system comprises a conductive metal rod, a heat pipe, a water-based cooling system, and/or a refrigerant-based cooling system (for example, a heat pump). In one embodiment, the cooling system comprises a heat pipe that transfers excess heat to an external heat sink. In one embodiment, the heat sink is air-cooled. In another embodiment the heat sink is liquid-cooled, for example a water block. In one embodiment, the cooling system comprises a liquid-based cooling system. In one embodiment, the cooling system comprises a water-based cooling system with a co-axial water pipe. In one embodiment the light source is affixed to the cooling system.

In one embodiment, the armature assembly comprises a light-transmissible tube (i.e., a light tube) and one or more structures that support the macroalgae in the growth chamber. In one embodiment, the armature assembly comprises a lid affixed to the light tube, wherein the lid creates a substantially air-tight and water-tight seal with the chamber assembly when the device is assembled and in use. In one embodiment, the armature assembly lid is removably affixed to the light tube. In one embodiment, the lid of the armature assembly comprises an effluent port where water leaves the bioreactor to return to the main tank or aquaculture system. In another embodiment, the support structures of the armature assembly comprise one or more of baffle plates, axially radiating pins, axially radiating blades, and/or flexible coils. In one embodiment, the one or more support structures of the armature assembly comprise baffle plates movably affixed to the light tube.

In one embodiment, the chamber assembly comprises a cylindrical outer housing and a base plate attached to the lower end of the outer housing. In one embodiment, the base plate comprises a supply port where water from the aquarium or aquaculture system enters the growth chamber when the device is in operation.

The present invention also features methods for maintaining the nutrient balance in an aquarium or aquaculture system using the bioreactor of the present invention comprising providing macroalgae into the growth chamber of the bioreactor; providing water from the aquarium or aquaculture system at a substantially steady flow rate while the bioreactor is in use, providing nutrient supplements; providing light from the bioreactor light source; and periodically removing and discarding a portion of the macroalgae. In one embodiment, the macroalgae is a green macroalgae, brown macroalgae or red macroalgae, or combinations thereof. In one embodiment the macroalgae is a green macroalgae. In a further embodiment, the green macroalgae is a species selected from the genuses *Chaetomorpha* and *Cladophora*. In one embodiment the green macroalgae is selected from the genus *Chaetomorpha*, and in a further embodiment the macroalgae is *Chaetomorpha linium*.

In one embodiment the light source is cycled on and off such that dark/light cycle of the bioreactor is substantially reversed in comparison to the dark/light cycle of the main tank or aquaculture system. If the main tank or aquaculture system does not contain photosynthetic organisms, the light/dark cycles of the main tank or aquaculture system can be shortened so that there are, for example, 3 or 4 light/dark cycles in a 24 hour period.

In one embodiment, one or more nutrients are supplemented in amounts sufficient to cause limitation of a targeted nutrient due to biological demand of the macroalgae. In one embodiment nutrients are supplemented so that phosphorus is the growth-limiting nutrient for the macroalgae in the bioreactor. In one embodiment, nitrogen is supplemented to maintain a nitrate to phosphate ratio of about 20:1 to 200:1 by weight. In one embodiment, nitrogen is supplemented to maintain a nitrate to phosphate ratio of about 80:1 to 120:1 by weight. In one embodiment, nitrogen is supplemented to maintain a nitrate to phosphate ratio of about 100:1 by weight.

DETAILED DESCRIPTION

The present invention provides devices and methods for the bioabsorption of operator-targeted excess nutrients in order to maintain a nutrient balance in an aquarium or aquaculture system that facilitates growth and/or health of one or more of the organisms that reside therein.

Figure 3:
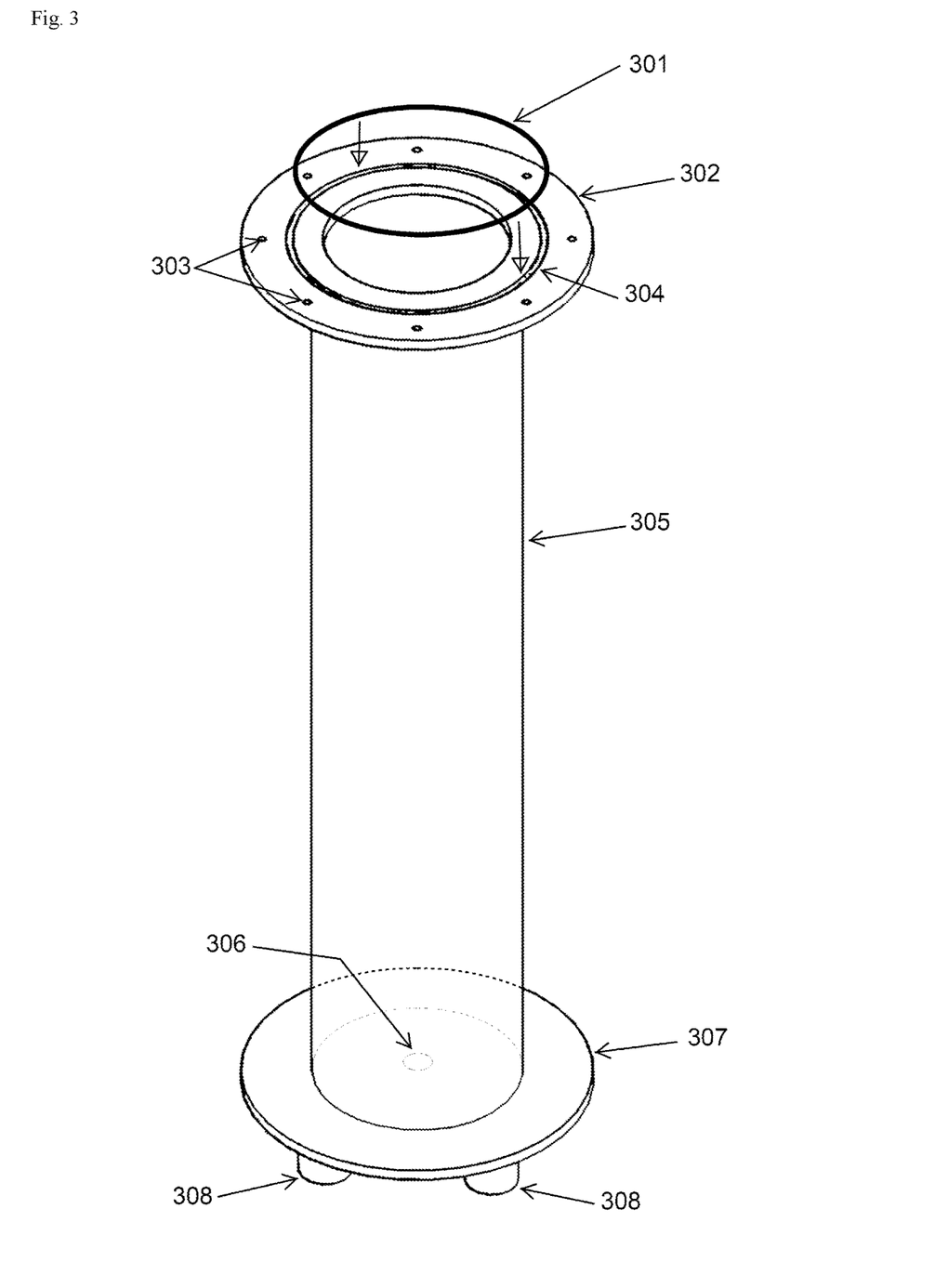
FIG. 3. One embodiment of the chamber assembly.
Figure 4A:
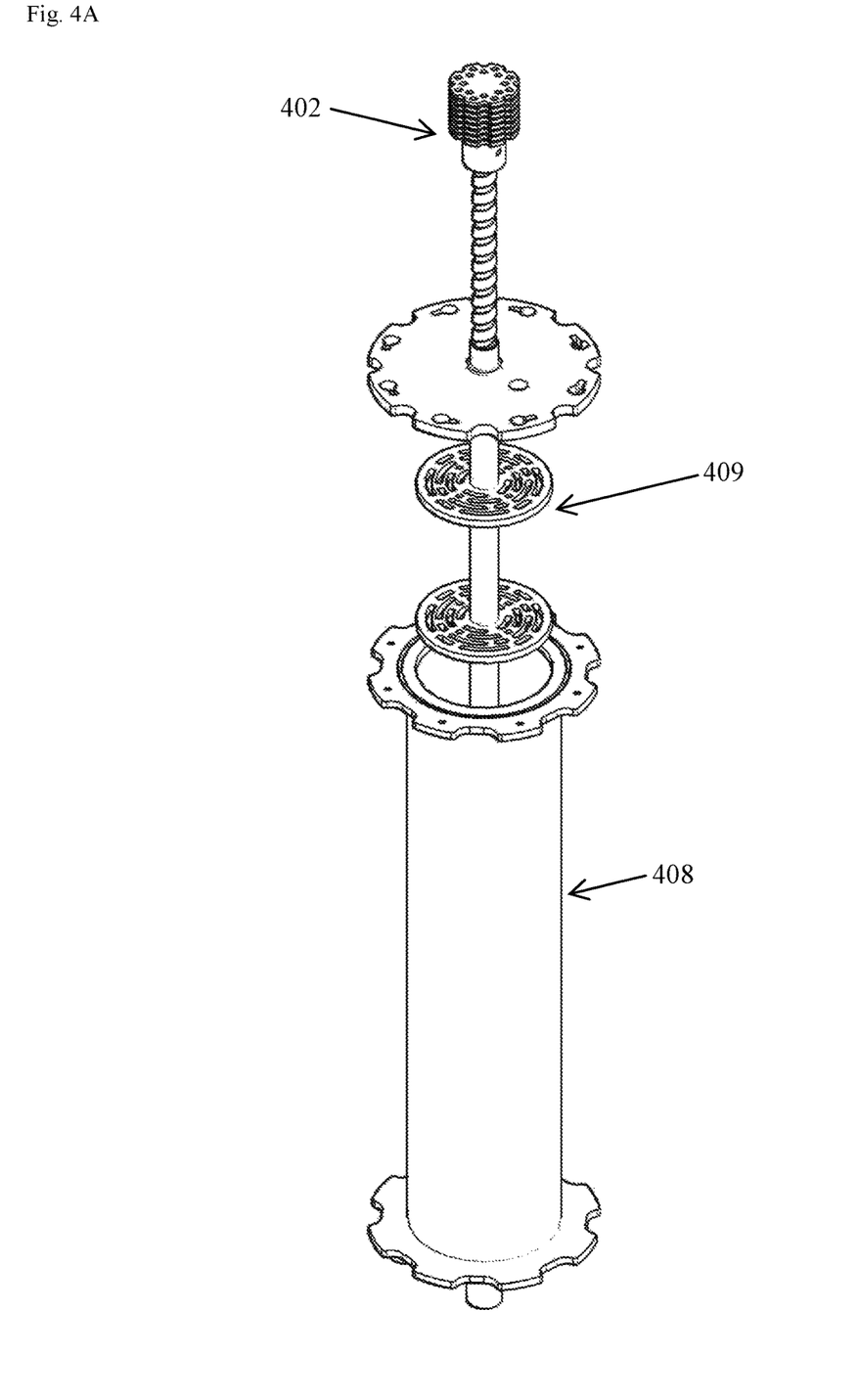
FIG. 4A. A schematic of the assembly of one embodiment of the bioreactor of the present invention with the light source assembly from FIG. 1, armature assembly from FIG. 2 and chamber assembly from FIG. 3.
Figure 4B:
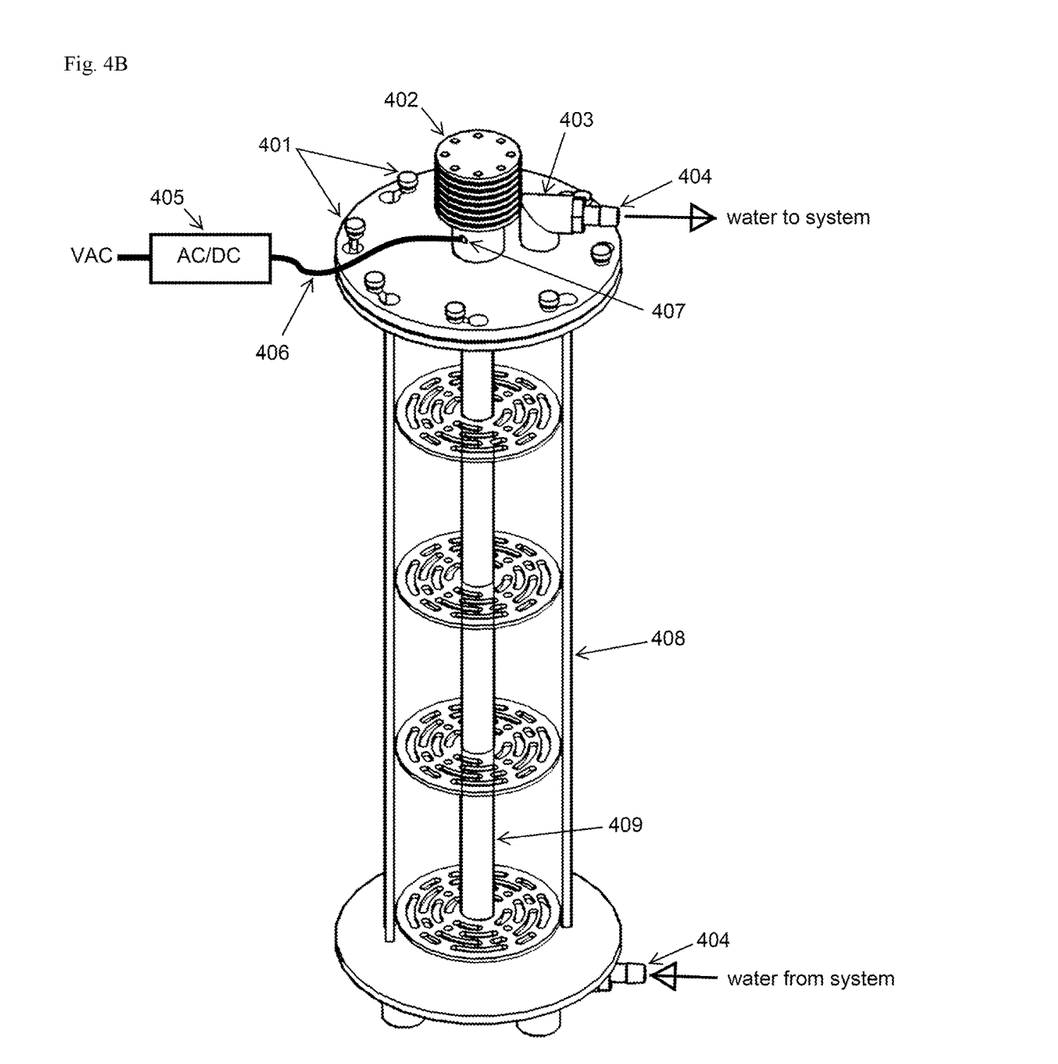
FIG. 4B. One embodiment of the assembled bioreactor with the light source assembly from FIG. 1, armature assembly from FIG. 2 and chamber assembly from FIG. 3.

The invention provides a bioreactor for the growth of macroalgae. The bioreactor of the present invention comprises three components: (i) the light assembly (see, e.g., FIG. 1); (ii) the armature assembly (see, e.g., FIG. 2); and (iii) the chamber assembly (see, e.g., FIG. 3). FIG. 4 shows the assembled bioreactor according to an illustrative embodiment of the present invention. One embodiment of the present invention is presented in FIG. 5, which provides a diagram of the incorporation of the bioreactor of the present invention in an aquarium system.

Light Assembly

Figure 1:
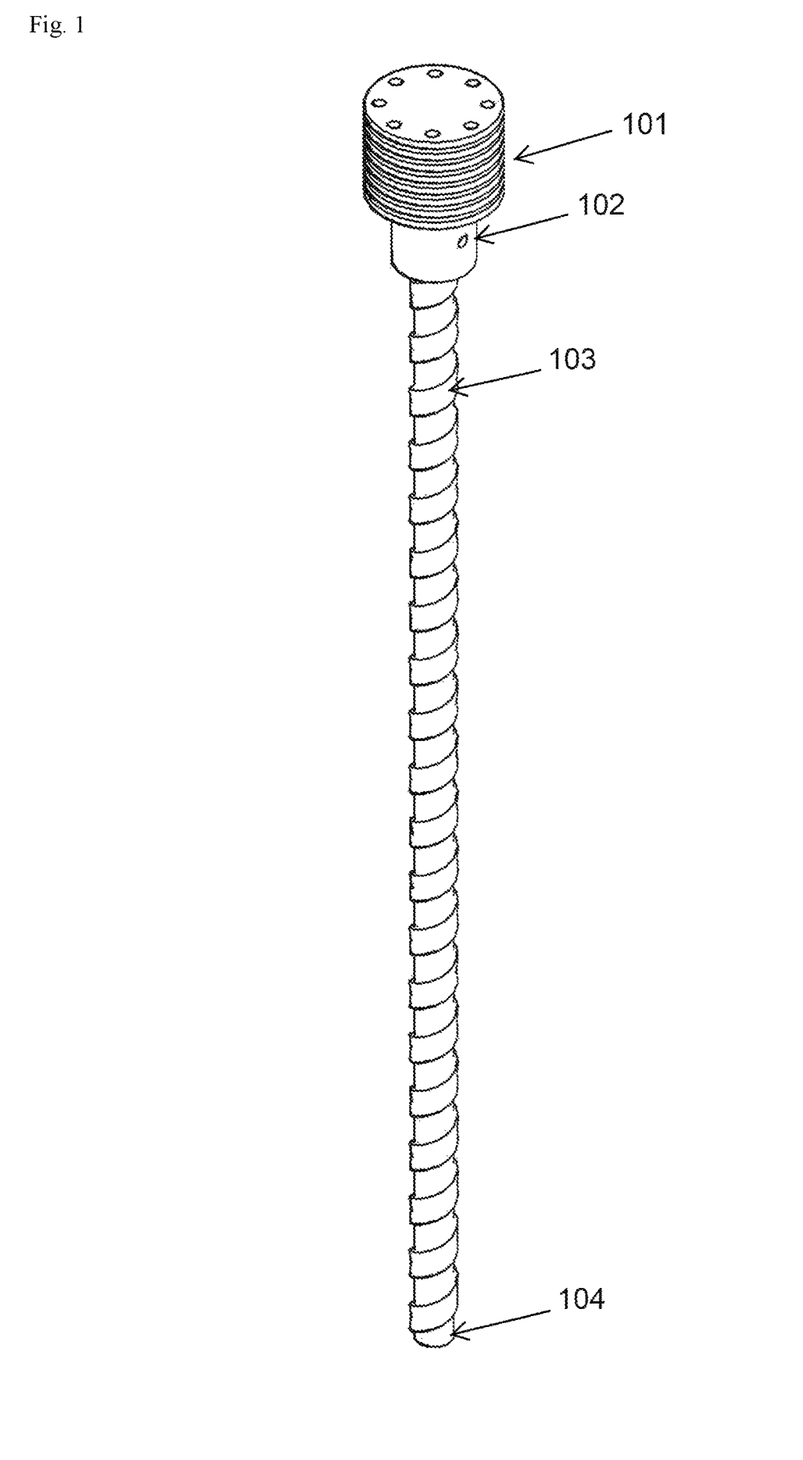
FIG. 1. One embodiment of the lighting assembly.

One aspect of the present invention includes a light assembly that emits light to support the growth of the macroalgae and a cooling system to remove heat generated by the light source. In a preferred embodiment, the light source is located within the growth chamber and has a coaxial orientation with respect to the growth chamber. FIG. 1 shows one embodiment for the light assembly where the light source 103 comprises a plurality (i.e., two or more) of LED lights. The power cord port for the light source is indicated by 102. In one embodiment, the plurality of LED lights are a LED ribbon (LED flexible array with thermally conductive adhesive backing). In one embodiment, the plurality of LED lights emit light at approximately the same wavelength. In another embodiment, the plurality of LED lights comprises two or more types of LEDs that each emit light at different wavelengths. For example, the plurality of LED lights that comprise the light source can include LEDs that emit predominately at about 450 nm wavelength light and LEDs that emit at about 650 nm wavelength light. In one embodiment, one set of LED are cool white LEDs (approximately 6500 k) having a spectral curve with a peak at about 450 nm and an even curve incorporating from about 550-650 nm, and the second set of LEDs emitting red light (about 625-660 nm). In one embodiment LEDs are selected based on the wavelengths of light emitted in order to optimize the growth of the macroalgae. Selection of wavelengths, for example, can be based on the absorption spectrum of the pigments used by the macroalgae in photosynthesis. In green algae, such pigments include chlorophyll, carotenes, phycocyanin, and xanthophylls. In red algae, the pigment includes phycoerythrin, and in brown algae, fucoxanthin. In one embodiment the light source emits light at an intensity of about 100 to about 350 $\mu mol/m^2/s$ at a distance of 1 inch. In other embodiments the light source emits light at an intensity of about 200 to about 300 $\mu mol/m^2/s$ at a distance of 1 inch. In one embodiment the light source emits light at an intensity of about 220 to about 260 $\mu mol/m^2/s$ at a distance of 1 inch. In one embodiment the light source emits light at an intensity of about 240 µmol/m$^2$/s at a distance of 1 inch.

In one embodiment, the LED light source 103 is affixed to a cooling system, which comprises a heat transfer device 104, which transfers heat generated by the light source to a heatsink 101 or other heat removal device. In one embodiment, the heat transfer device is a heat pipe. In another embodiment, the heat transfer device comprises a conductive metal (e.g., aluminum) rod. In one embodiment, the cooling system is used to cool the light assembly to, e.g., below ambient temperatures. In one embodiment, the LED light source is affixed to the heat transfer device (e.g., a heat pipe) using optically clear PET heat shrink tubing (not shown in FIG. 1). In one aspect of the present invention, the light source of the light assembly is enclosed in a light-transmissible submersible housing (e.g., a light tube).

In one embodiment, the heat transfer device has a hollow interior, and is shaped, for example, like a hollow cylinder, hollow triangular prism, hollow rectangular prism, a hollow octagonal prism and the like. The hollow portion of the heat transfer device may comprise a supply line to transport the water entering the bioreactor to the bottom of the growth chamber. In one embodiment, the heat transfer device comprises multiple flat heat pipes arranged to form a hollow multisided polyhedron, for example, a hollow triangular prism, hollow rectangular prism, a hollow octagonal prism and the like. In one embodiment, the heat transfer device comprises an arrangement of flat heat pipes having 5 to 10 sides. In one embodiment, the heat pipe is in the shape of a coiled ribbon. In one embodiment, a light source (for example an LED array) is affixed to one or more of the flat heat pipes.

Figure 6:
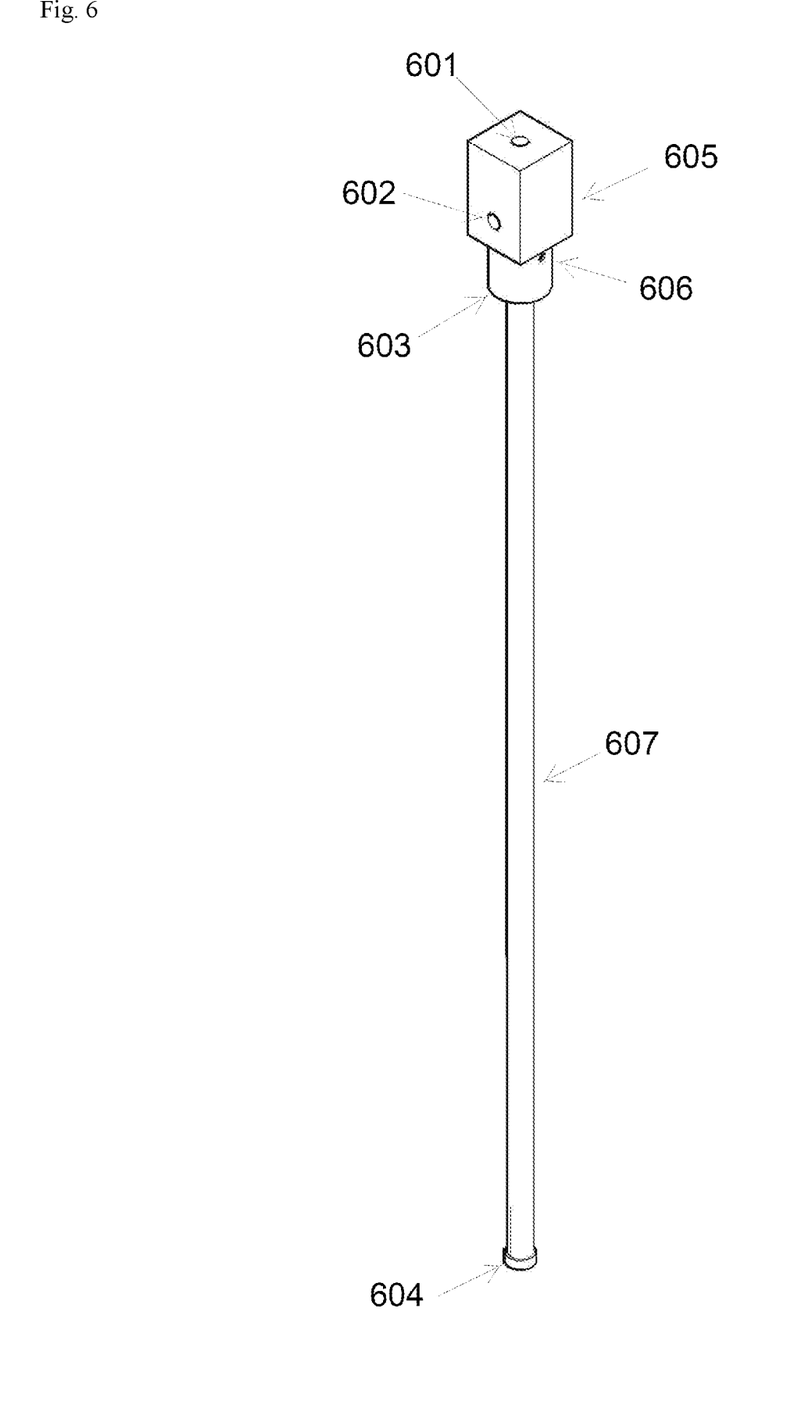
FIG. 6. A diagram of one embodiment for a water-based cooling system for use in the lighting assembly.
Figure 7:
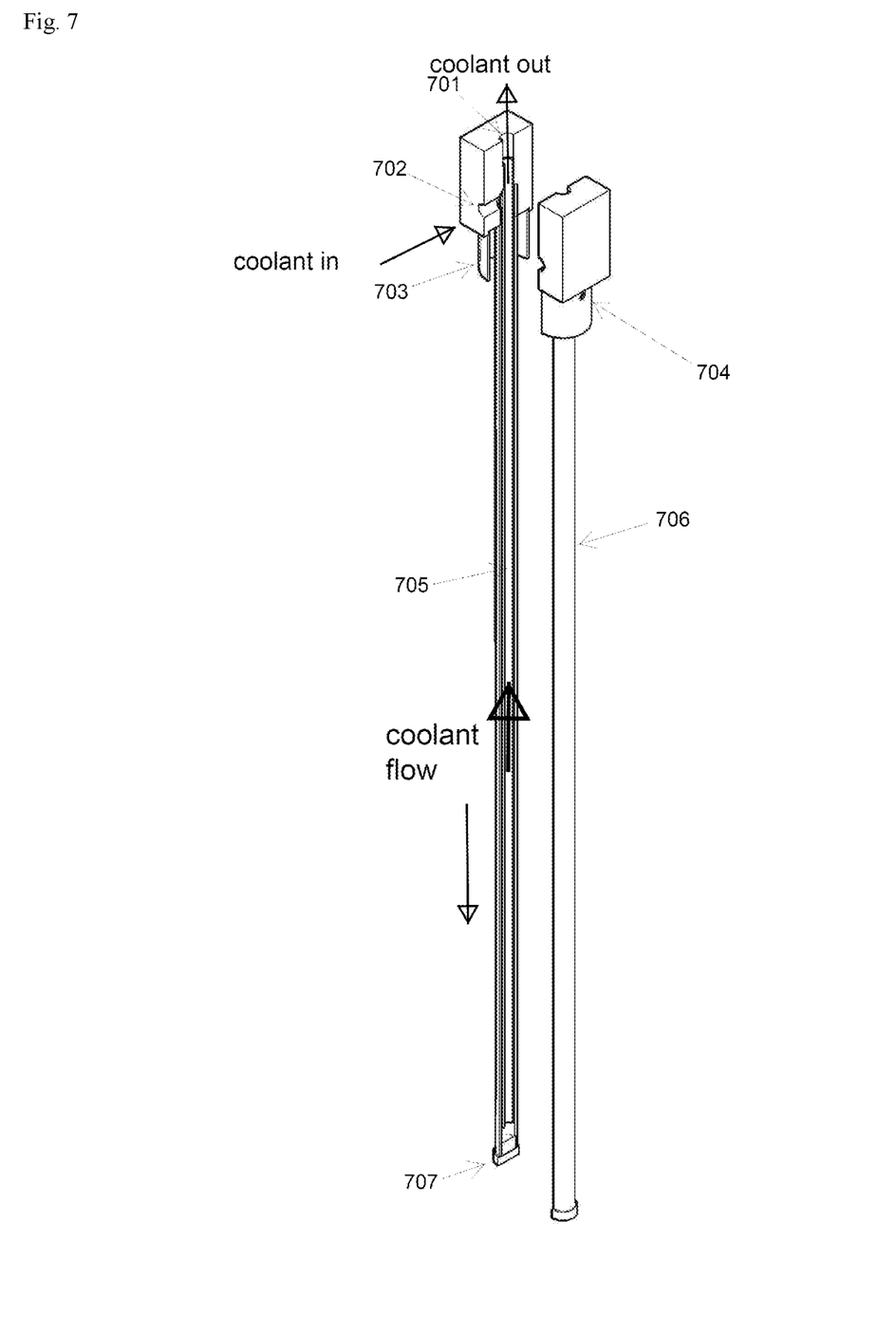
FIG. 7. A cross sectional diagram of one embodiment for a water-based cooling system for use in the lighting assembly.
Figure 8:
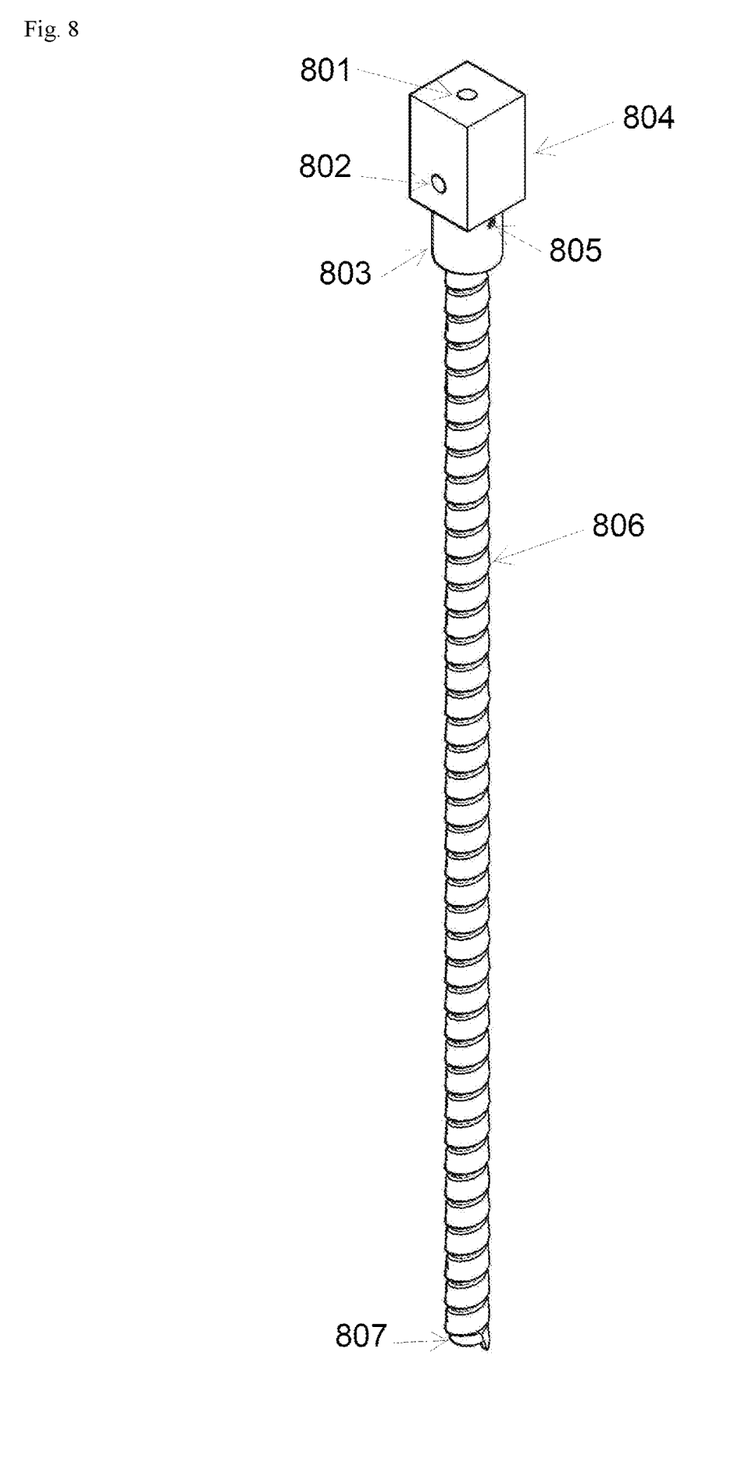
FIG. 8. A diagram of a one embodiment of a lighting assembly using a water-based cooling system.

In one embodiment, the light assembly cooling system comprises a liquid-based cooling system. FIGS. 6-8 provide one embodiment of a water-based cooling system for use in devices of the present invention. FIG. 6 provides a diagram of the water-based cooling system, which is also displayed in FIG. 7 as a cross sectional diagram. FIG. 8 provides a diagram of the water-based cooling system as part of a lighting assembly comprising a LED ribbon as the light source. In this embodiment, water, or other appropriate coolant, is circulated by a pump from a radiator into a manifold, and then by flexible tubing into a water block 605 (804 in FIG. 8) that contains a co-axial coolant tube assembly by an appropriate port 602 (702 in FIG. 7, 802 in FIG. 8) such as a NPT threaded port. The water continues down a co-axial coolant tube 607, which comprises an inner coolant tube 705 and an outer coolant tube 706 that carry the coolant the length of the coolant tube and back to the water block. The coolant tube is capped at the distal end by an endcap 604 (707 in FIG. 7, 807 in FIG. 8). The coolant leaves the water block by an appropriate port 601 (701 in FIG. 7, 801 in FIG. 8) such as a NPT threaded port and returns by flexible tubing to a manifold and back to the radiator, giving up the collected heat. The water block, coolant tube, and endcap may be independently composed of any appropriate heat-conducting material, for example, aluminum or copper. An adapter tube 603 (703 in FIG. 7, 803 in FIG. 8) can be used to center the lighting assembly in the light tube of the armature assembly. The adapter tube may have a power cord grommet hole 606 (704 in FIG. 7, 805 in FIG. 8) through which the power cord for the light source passes. In one embodiment, one or more LED ribbons 806 are affixed to the exterior of the co-axial coolant tube 607. This embodiment of the light assembly cooling system is useful when multiple bioreactors of the present invention are used in parallel; on large systems; where it is desirable to collect and store the generated heat for other uses; or where heat needs to be directed out of the enclosure where the bioreactor resides.

In one embodiment, the light source is a fluorescent bulb, for example a T5 fluorescent bulb. When fluorescent bulbs are used it is often desirable to use polycarbonate light tubes that are more resistant to the generated heat than, for example, those made from acrylic, which may manifest stress fractures, resulting from the thermal cycling of the lights when they are turned on and off for the periodic light/dark cycle. In one embodiment, the fluorescent light source is a cold cathode fluorescent bulb. In other embodiments, the light source comprises a light emitting cathode (LEC) or side emitting fiber optics.

Armature Assembly

Figure 2:
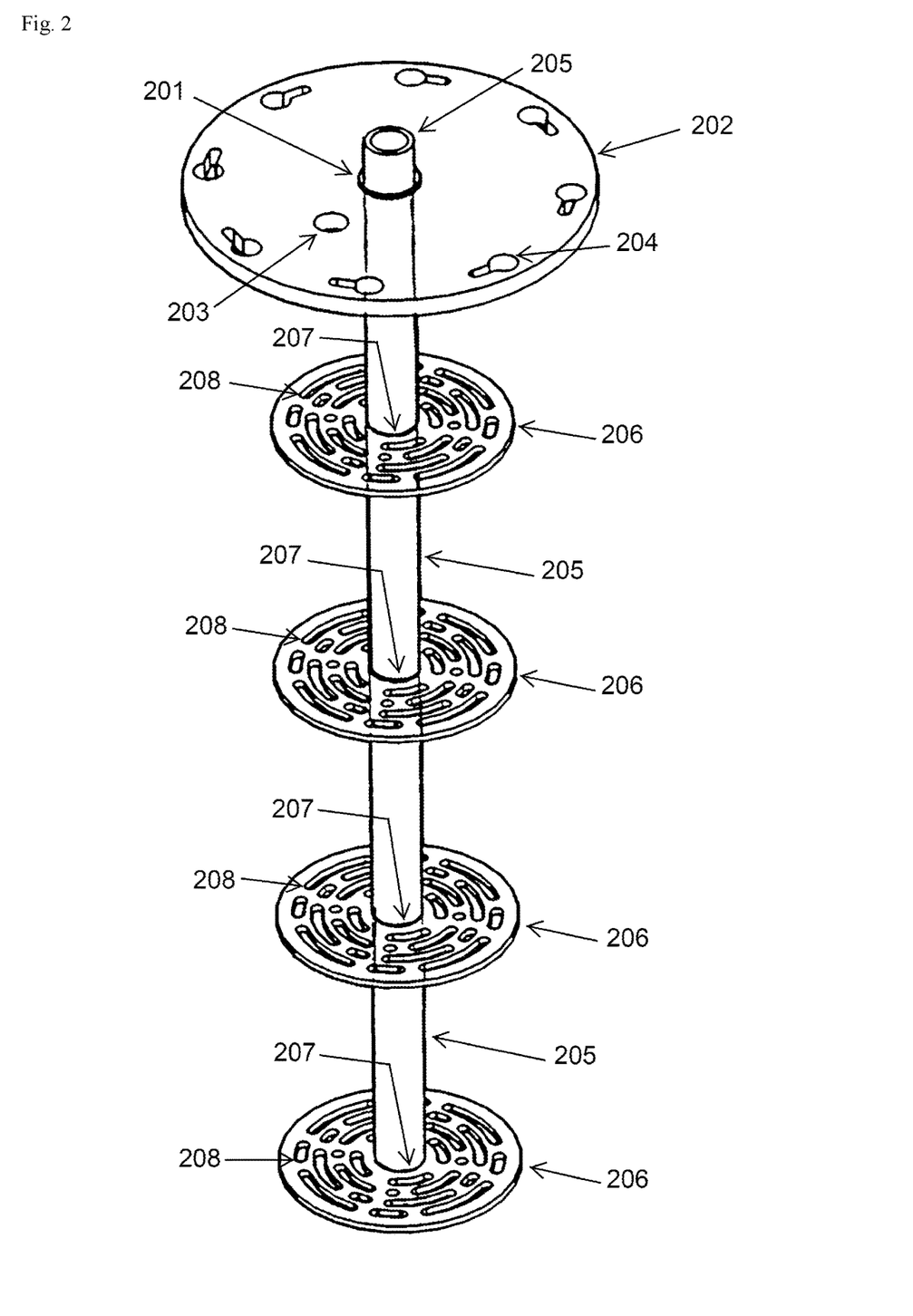
FIG. 2. One embodiment of the armature assembly.

A second component of the present invention is an armature assembly, an embodiment of which is provided in FIG. 2. In one embodiment, the armature assembly comprises a tube of light-transmissible material 205 (referred to herein as the light tube) open on one end (referred to herein as the top end) and capped on the other. The open end of the light tube 205 receives the light source (103 from FIG. 1) from the light assembly as shown in FIG. 4. The light tube has a sufficient diameter to house the light source from the light assembly. The light tube may be comprised of an appropriate light transmissible material. In one embodiment the light tube comprises polycarbonate. In a further embodiment, the light tube 205 is removable from the armature assembly allowing for replacement of the light tube if the tube has, e.g., yellowed over time due to exposure to light from the light source 103.

The armature assembly has one or more support structures as a scaffold to support the growth of the macroalgae. In one embodiment, the support structure(s) comprise diffuser (or baffle) plates 206, affixed to the light tube 205, that separate the growth chamber into one or more sections and supports and contains individual masses of the macroalgae. Each diffuser plate comprises a plurality of holes 208 that allow the flow of water through the growth chamber. In a preferred embodiment, the diffuser plates 206 are movably affixed to the light tube. In one embodiment, the diffuser plates are held in place along the light tube by o-rings 207 (one above and one below each diffuser plate). In another embodiment, an expanding gasket is used to position each diffuser plate. The diffuser plates can be made out of any suitable material including plastics like acrylic. In another embodiment, the diffuser plates comprise a mesh screen. The top and bottom diffuser plates contain the algae within the bioreactor. In one embodiment the support structures comprise one or more axially radiating pins or blades in a propeller design with the hub encircling the light tube. When made of light transmittable material, such structures act to redirect light deep into the algae mass. In one embodiment, the support structures comprise a plurality of tightly spiraled flexible coils (e.g. cable management wrap) that stretch vertically from the base to top plate. In this embodiment, macroalgae is affixed by pinching it between the coils of the spirals.

In one embodiment, at the top end of the armature assembly is a lid 202 affixed to the light tube 205. In one embodiment, the lid is removably affixed to the light tube to facilitate replacement of the light tube, if, for example, the light tube has yellowed due to exposure to light from the light source. To facilitate a tight seal between the lid 202 and light tube 205, a sealing device 201 may be used, for example an expanding rubber gasket (Uniseal). When assembled, the armature assembly is fastened via the lid 202 to the flange of the chamber assembly (302 shown in FIG.

3). The lid 202 can be fastened to the chamber assembly by any mechanism that allows for the periodic disassembly of the armature assembly from the chamber assembly. In one embodiment the lid comprises keyholes 204 that allow the lid to be fastened to the chamber assembly using thumb screws (401 in FIG. 4). In another embodiment the lid is reversibly fastened to the chamber assembly using one or more fasteners or clamps. In another embodiment, rather than a flange, the lid is reversibly affixed to the chamber assembly using a large threaded union fitting. The lid seals the top of the bioreactor when assembled and in use from the surrounding air atmosphere and forms a water-tight seal. The lid further comprises an effluent port 203, by which the water leaves the bioreactor and returns directly or indirectly to the main tank. The effluent port may comprise a National Pipe Taper (NPT) or other suitable adapter including cam lock, hose barb, threaded union, push connect tube fittings, valved quick disconnects (e.g., CPC; Colder Products Connector), and the like. Selection of the adapter can depend on the type of liquid transfer conduit used, pressure, and flow rate.

Chamber Assembly

A third component of the device of the present invention is a chamber assembly, an embodiment of which is shown in FIG. 3. The chamber assembly comprises an outer housing 305. In a preferred embodiment, the outer housing is cylindrical, however, other shapes including for example cone, cube, and rectangular prism are also contemplated (with an appropriate adjustment to the shape of the diffuser plates). The outer housing can be composed of any suitable material, including for example acrylic, PVC, polyethylene, polypropylene, PET, ABS, PTFE, FEP, or any polymer with low water absorption rates that are substantially nonreactive, preferably FDA approved with low to no plasticizers that may leach into the system water. The outer housing may also be composed of metal, for example, stainless steel, titanium, or other substantially non-reactive metal, or a metal that is coated with a polymer. The bottom end of the chamber assembly comprises a base plate 307 attached to the bottom edge of the outer housing 305. In one embodiment, the base plate comprises a supply port 306 for the water entering the bioreactor. Alternatively, water entering the bioreactor can enter through the lid and travel down a supply line to the bottom of the growth chamber. In one embodiment, the supply line runs to the bottom of the growth chamber as part of the light assembly, for example down the center of a hollow heat transfer device. The bottom of the base plate may also comprise one or more standoffs 308 to elevate the base plate 307 from a surface. In one embodiment, the top end of the outer housing 305 is attached to a flange 302 for fastening the chamber assembly to the lid (202 in FIG. 2) of the armature assembly. In order to seal the interior of the reactor from the atmosphere and to prevent water leaks, the flange 302 further comprises a device for creating an airtight and water tight seal when the bioreactor unit is assembled and in use. In one embodiment, the flange 302 comprises an o-ring gland 304 in which an o-ring 301 is seated. In one embodiment, the flange 302, further comprises threaded holes 303 for receiving thumb screws (401 in FIG. 4) to secure the lid 202 of the armature assembly to the flange 302 of the chamber assembly.

Assembled Bioreactor

FIG. 4A shows a schematic of the assembly of one embodiment of the bioreactor of the present invention. FIG. 4B shows one embodiment of the assembled bioreactor of the present invention. The light source (103 from FIG. 1) from the light assembly 402 (see also FIG. 1) is inserted into the light tube (205 from FIG. 2) of the armature assembly 409 (see also FIG. 2). The armature assembly is inserted into the outer housing (305 from FIG. 3) of the chamber assembly 408 (see also FIG. 3). Water enters the bioreactor from the aquarium or aquaculture system via a port 404 located at, or near, the bottom of the reactor (see 306 in FIG. 3). Water leaves the bioreactor via a second port 404 at, or near the top of the system (see 203 in FIG. 2). In one embodiment each entrance and exit port comprises an appropriate fitting (for example, a hose barb) for attaching the hoses to carry water from and to the rest of the system. In a preferred embodiment the entrance and exit ports comprise appropriately valved (to minimize spills during maintenance) quick disconnects (for example CPC) for attaching and detaching the inlet and outlet hoses to the inlet and outlet ports.

The light source (103 from FIG. 1) from the light assembly 402 is powered by an appropriate power source 405, for example, an AC/DC transformer. LED strips may, for example, require 12 vdc switching power supply, while others require a 24 vdc switching power supply. The power source is connected to the light assembly 402 by a wire harness 406, that enters the light assembly through a wire grommet 407. When a fluorescent bulb is used as the light source, a wire harness connects both ends of the fluorescent bulb to a remote ballast.

The growth chamber (where growth of the macroalgae occurs) is bounded by the interior surface of the outer housing 305 of the chamber assembly and the exterior of the light tube 205 from the armature assembly when the device is assembled. The diameter of the growth chamber allows for optimal growth of the macroalgae. The portions of the macroalgae located farther from the light source receive less light due to shading by the macroalgae nearer the light source. Growth of the macroalgae along the length of the growth chamber provides continued exposure to maximum lighting, which facilitates growth of the macroalgae, removal of excess nutrients (for example phosphates or carbon (e.g., $CO_2$, carbonic acid, etc.)), and super-saturation of the water with oxygen.

The optimal diameter of the growth chamber depends upon the light penetration through the macroalgal mass. For *Chaetomorpha* macroalgae, such as *Chaetomorpha linium*, the radius of the growth chamber (as measured from the exterior of the light tube 205 to the interior of the outer housing 305) is greater than about 1 inch and less than about 5 inches. In a preferred embodiment the radius of the growth chamber is about 2 inches to about 4 inches. As the diameter of the growth chamber increases, the water velocity decreases and hydraulic retention times increase for the same volume of water being pumped. Preferably, the inside diameter of the growth chamber is about 4 to about 10 inches (with the outside diameter of the light tube being about 1 inch). In a preferred embodiment, the inside diameter of the growth chamber is about 5 inches. The optimal flow rate through the bioreactor depends on the dimensions of the bioreactor. The minimum flow rate through the bioreactor should allow the macroalgae closest to the exit to grow at substantially the same rate as the macroalgae closest to the water entrance to the bioreactor growth chamber. Optimal flow rate of water through the growth chamber is approximately no more than 10% higher than this minimum flow rate. In one embodiment, the inside diameter of the growth chamber is about 5 inches and the flow rate of water through the growth chamber is about 150 to about 350 gallons per hour (gph), and preferably about 180 to about 250 gph. In another embodiment the flow rate is about 200 to 300 gph. In another embodiment the flow rate is about 250 gph. In another embodiment the flow rate is about 300 gph. The flow rate can be increased or decreased in bioreactors of the present invention depending upon the diameter of the growth chamber. For bioreactors with a diameter of 8 inches, flow rates can be between about 400 gph to about 1200 gph, and preferably about 400 to about 600 gph. In one embodiment the flow rate is about 600 gph to about 1,000 gph. In another embodiment, the flow rate is about 700 gph to about 800 gph when the diameter of the growth chamber is about 8 inches. In one embodiment, the inside diameter of the growth chamber is 4 inches and the flow rate of water through the growth chamber is about 100 to about 250 gph, preferably about 150 to about 200 gph.

Figure 5:
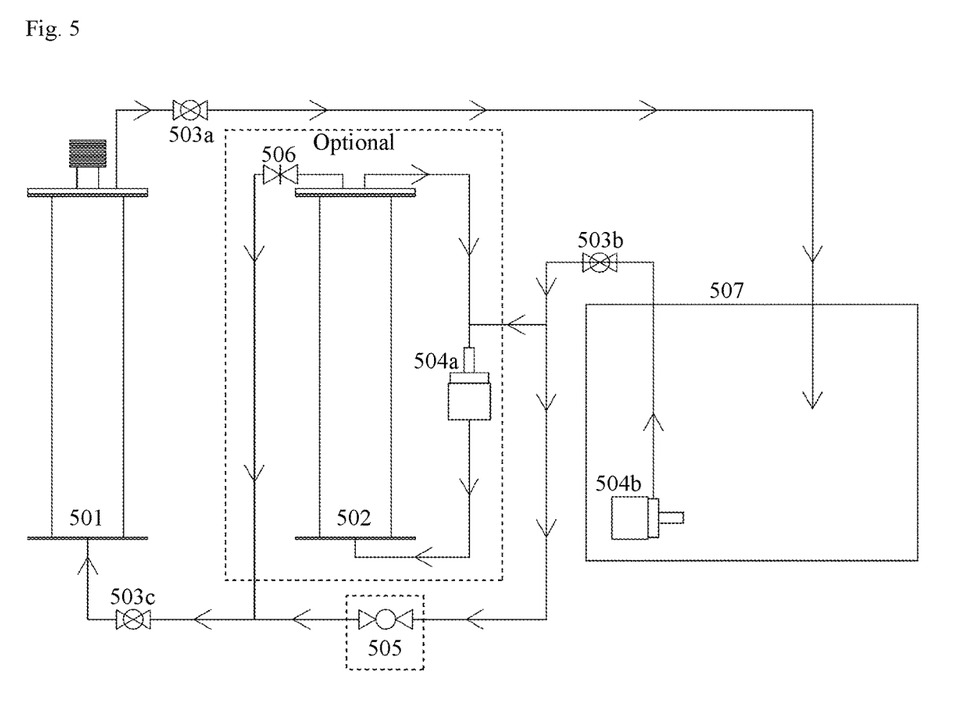
FIG. 5. Schematic view of the bioreactor of the present invention as part of a marine aquarium system.

FIG. 5 provides a diagram of the bioreactor of the present invention as part of a marine aquarium system. Water is pumped from a sump or main tank 507 by a pump 504b that provides water flow to the bioreactor of the invention 501 and optionally to a calcium reactor 502. A valve, for example a ball valve or globe valve, 503a controls the flow rate through the bioreactor and creates back pressure. In addition, an optional throttling valve 503b, for example a ball valve or globe valve, can be added to control flow. An additional valve 503c shuts down water flow to the bioreactor 501. In one embodiment of the invention, the flow rate through the bioreactor is maintained at a substantially steady flow rate so that no water surge motion is utilized while the system is running.

In one embodiment, the bioreactor of the present invention is used downstream of a calcium reactor 502. A portion of the water is diverted to the calcium reactor and through a recirculating pump 504a before entering the calcium reactor. A valve 506 (e.g., a needle valve) controls the rate of effluent leaving the calcium reactor and entering the bioreactor of the present invention. The flow rate of the calcium reactor effluent controls the calcium to carbonate ratio in the reef tank. A valve, for example a globe valve, 505 is used to create a pressure difference so water flows through the calcium reactor.

Figure 9:
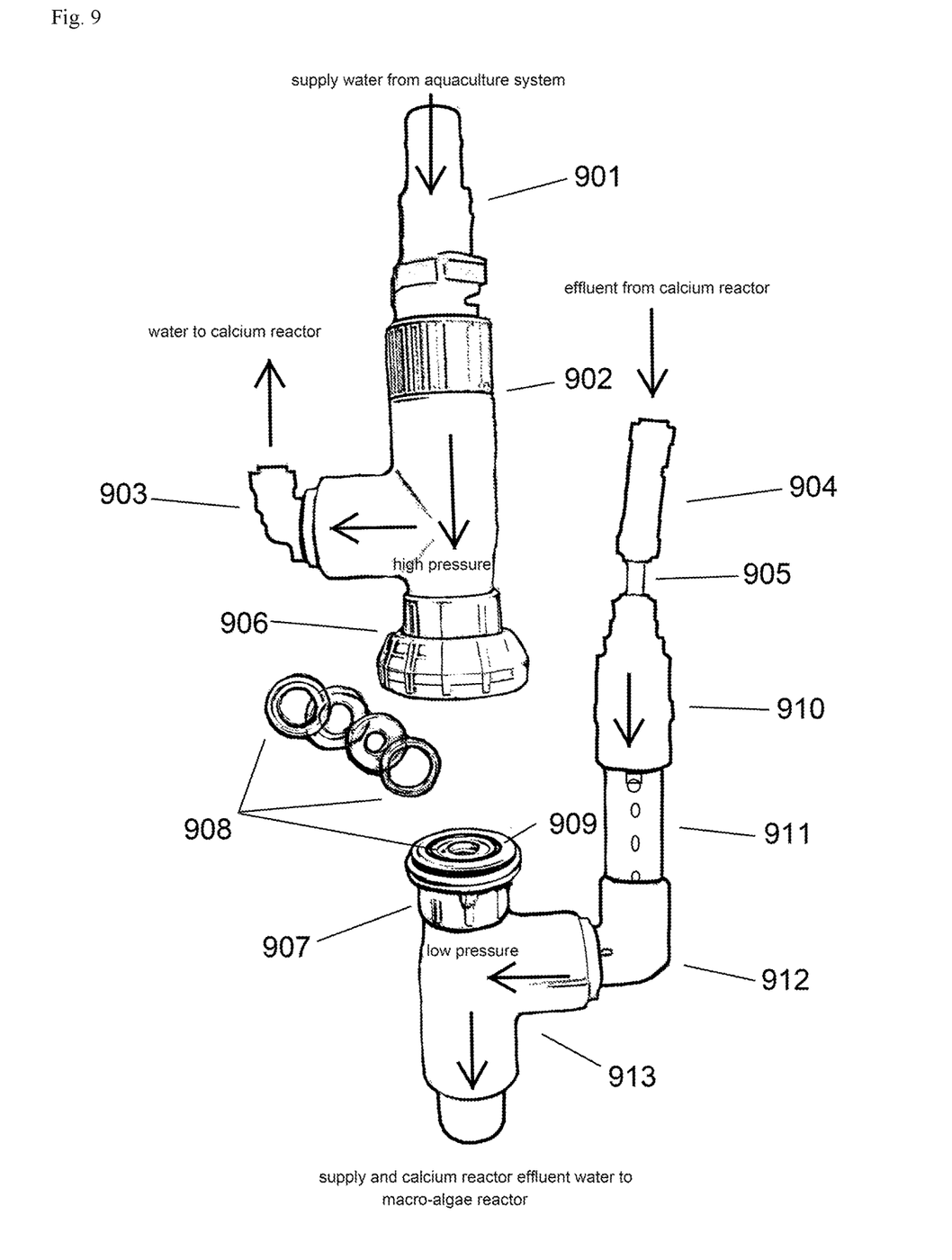
FIG. 9. A diagram of a calcium feed and injection assembly used to divert water from the aquarium or aquaculture system to a calcium reactor before entering the bioreactor of the present invention.

In one embodiment, a calcium feed and injection assembly (FIG. 9) is used to divert a portion of the water from the aquarium or aquaculture system to a calcium reactor before the water enters the bioreactor of the present invention. Aquaculture system water enters the calcium feed and injection assembly through port 901 (e.g., a quick disconnect barb fitting) where it enters the tee fitting 902. Water pressure builds up in the tee fitting due to the restrictor assembly (906, 907, 908, 909) causing some water to be diverted under pressure through the elbow 903 to the system's calcium reactor. The balance of flow to the macro-algae bioreactor and back pressure required to supply water to the calcium reactor is achieved by the restrictor assembly, which comprises a female threaded union half 906, a male threaded union half 907, restrictor disks 908, and an o-ring 909 to prevent leaks when the restrictor assembly is in use. Restrictor discs 908 of different orifice diameters can be swapped out of the restrictor assembly by the operator to match the pressure and flow curve of the supply water. A drip counter assembly (910, 911, 912) allows the operator to determine which restrictor disk provides proper back pressure and flow to the calcium reactor. The drip counter assembly comprises a drip counter head 910, a clear drip counter body 911, and a drip counter elbow 912. A restrictor disk 908 with a proper sized orifice that provides a steady flow of calcium reactor effluent can be determined by observing flow through the drip counter body 911. To make the flow rate visible, trapped air is kept in the drip counter body 911 by preventing its escape by the vertical orientation of the drip counter body 911 and the use of a check valve 904 (e.g., a push connect check valve) to prevent the air from back-flowing into the calcium reactor when the supply water is turned off for periodic maintenance intervals. The check valve 904 can be connected to the drip counter head by, for example, tubing 905. Effluent from the calcium reactor recombines with the supply water from the aquaculture system in the low pressure area of the tee fitting 913 and then flows into the macro-algae reactor. This mixture containing the calcium reactor effluent is laden in carbon dioxide and excess phosphate. These excess nutrients are assimilated into the biomass of the growing macro-algae in the bioreactor, greatly reducing the amount of carbon dioxide and phosphate reaching the rest of the aquarium or aquaculture system where these nutrients may fuel the growth of nuisance organisms or accumulate to levels that may hinder the growth of the desirable organisms contained within.

Calcium reactors are used to maintain calcium, carbonate and trace element levels. Calcium reactors contain a calcium-based substrate such as aragonite or limestone which is dissolved by injecting $CO_2$ under pressure into the calcium reactor chamber converting it to carbonic acid. The calcium and trace elements liberated by the calcium reactor are used mainly by calcareous organisms such as stony corals, encrusting algae, and shell bearing mollusks. However, excess carbonic acid from the calcium reactor can lower the pH of the system, especially when the main system's lights are off because photosynthesis has ceased. The aragonite or limestone used also contains bound phosphate that is liberated when dissolved. Passing the effluent from the calcium reactor into a bioreactor of the present invention before the water reaches the main tank allows the macroalgae contained therein the opportunity to absorb the excess carbon dioxide (carbonic acid) and phosphate before it reaches the main tank where it could build up.

For large aquariums or aquaculture systems, a main pump is used to feed water to multiple bioreactors of the present invention in parallel. In another embodiment, multiple bioreactors can be stacked end-to-end.

The present invention eliminates the need for a protein skimmer as part of the aquarium or aquaculture system. Protein skimmers (foam fractionators) equilibrate the tank dissolved gases in the same ratio as the atmosphere surrounding the system. The bioreactors of the present invention, however, can increase the ratio of dissolved oxygen to carbon dioxide, to greater than that of the surrounding atmosphere (after accounting for the partial pressures of both gases in seawater). Protein skimmers also export desirable nutrients by removing bacteria, zooplankton, and phytoplankton such as diatoms, which is food for many of the system inhabitants.

The present invention also eliminates the need for phosphate removers such as granulate ferric oxide (GFO), aluminum oxide, (zeolite), or other phosphate binders (e.g., lanthanum chloride). Through bioabsorption, phosphate is incorporated into the cells of the macroalgae as it produces ATP while growing. When the algae is harvested phosphate is exported out of the system. In addition, rinsing the biofilm off the algae removes additional nutrients from the system, including phosphate.

The present invention also eliminates any need for anaerobic denitrification using bacteria. Nitrate is absorbed by the growing macroalgae to produce, e.g., cellular proteins. During harvest of the macroalgae this nitrogen is exported out of the system. In one embodiment, a soluble nitrogen source is added because the nitrogen is generally absorbed at a higher rate than phosphate by the macroalgae.

In one embodiment, when in use, the bioreactor of the present invention is connected to the main tank or sump as part of a closed loop system, which is substantially isolated from the ambient air atmosphere. While the device is in operation, water circulating through the device has limited, or substantially no, direct exposure to the surrounding air. As a result, the macroalgae in the bioreactor are not exposed to carbon directly derived from the atmosphere and are dependent upon carbon derived from the main tank and its inhabitant's respiration. The atmospherically isolated system prevents the contained macroalgae from incorporating carbon directly from the air, which can lead to the synthesis of excessive dissolved organic carbon compounds (e.g., polysaccharides) that yellow the water. The bioreactor of the present invention captures excess carbon from tank inhabitants' respiration and releases dissolved oxygen. If carbonic acid or $CO_2$ become so limited, the macroalgae can utilize carbonate to fulfill its carbon requirements. In one embodiment, the bioreactor will also capture excess phosphate, provided nitrogen and other macro and trace elements are provided by the operator.

Macroalgae

Algae are photosynthetic, nonvascular plants that contain chlorophyll and have simple reproductive structures. The macroalgae used as part of the present invention are also called "seaweeds" due to their size and multicellular construction. Macroalgae are primarily found in the divisions *Chlorophyta* (green algae), *Phaeophyta* (brown algae), and *Rhodophyta* (red algae). Green algae (*Cladophorales*) are divided into two families, the Cladophoraceae, which are filamentous species, and the Anadyomenaceae, whose filaments are fused together to form blades. The Cladophoraceae are further divided into three genera: *Rhizoclonium* (more delicate, unbranched filaments, producing rhizoids), *Chaetomorpha* (coarse, unbranched filaments), and *Cladophora* (branching filaments). For a description of macroalgae see Clinton J. Dawes, Macroalgae, Chapter 6 in Marine Botany ($2^{nd}$ edition, 1998) incorporated herein by reference.

In one embodiment of the present invention, the macroalgae is green algae. In one embodiment the macroalgae used in the present invention is selected from the genus *Chaetomorpha*. In a further embodiment the macro algae is *Chaetomorpha linium*. In another embodiment, the macroalgae is selected from the genus *Cladophora*. In another embodiment, the macroalgae used in the bioreactor is a macroalgae from the genus *Boodlea*. In one embodiment of the present invention, the macroalgae does not attach, e.g., by holdfasts, to the growth chamber walls or diffuser plates.

Nutrient Supplements

The device and methods of the present invention manipulate the marine ecological stoichiometry of nutrients in the aquarium or aquaculture system. The process is controlled by altering the stoichiometric ratios of marine chemical elements, e.g., described by oceanographer, Alfred C. Redfield. These "Redfield Ratios" describe the average elemental composition of marine biomass found throughout the oceans. The Redfield Ratios describe a carbon (C): nitrogen (N): phosphate (P) stoichiometric ratio as 106:16:1. This stoichiometric ratio was later expanded to include other major marine elements.

By utilizing the devices and methods of the present invention, the amounts and ratios of elements in the aquarium or aquaculture system can be manipulated with the purpose of reducing the concentration of an operator-specified element, through absorption by a biological medium, in this case macroalgae. Control of one or more limiting nutrients is achieved by calculated increases in concentration of specific other elements in the aquaculture system. By providing the elements the macroalgae biologically requires except for one or more specified nutrient(s), those specified nutrient(s) are limited. For example, increasing the concentration of nitrogen in the system will lead to increased biomass until phosphate is exhausted. One way to express this is $N+P \leftrightarrows biomass$. This simplified equation can be expanded to include other biologically important elements $(light+water+C+N+P+K+Mg+B+Si+Mo+Fe+ \ldots \leftrightarrows biomass+O_2)$. In an aquarium system, biomass is added in the form of feed, which increases the amounts of elements in the system, but not typically at desirable ratios (e.g., Redfield ratios in marine systems). This uneven accumulation of elements in the system can lead to undesirable effects including poor growth of system inhabitants and the uncontrolled growth of nuisance organisms. The methods and devices of the present invention employ the use of elemental additions so that feed is primarily assimilated into the main tank's cultured organisms and remaining unused elements are absorbed by the macroalgae in the bioreactor, and ultimately removed during harvesting of the macroalgae.

In one aspect of the invention, the optimal growth of the macroalgae is facilitated, and the nutrient balance of the aquarium or aquaculture system is maintained, by the addition of nutrient supplements to the system. When the devices and methods of the invention are used to maintain tropical or sub-tropical reef aquariums, nutrients are added so that phosphate is the growth-limiting nutrient for growth of the macroalgae in the bioreactor. Growth of the macroalgae removes phosphate from the system, which when present at too high levels can interfere with the growth of corals.

Nitrogen in the form of nitrate ($NO_3$), ammonium ($NH_4$) or nitric acid ($HNO_3$) is supplemented as needed to maintain a ratio of nitrate to phosphate ($PO_4$) of about 20:1 to about 200:1 and preferably between about 80:1 to about 120:1 (by weight). In one embodiment, nitrogen is supplemented to achieve a ratio of about 100:1 nitrate to phosphate. Below a ratio of about 16:1 nitrate to phosphate (i.e., 16 ppm nitrate to 1 ppm phosphate), the system is considered nitrogen limited. Typical levels in seawater are about 0.02-0.07 ppm phosphate and about 0.1-2.5 ppm nitrate. In one embodiment of the present invention, ammonium nitrate 5% solution is used as needed (based on test results) to raise the nitrate level. Addition of 1 ml of the 5% (w/v) ammonium nitrate solution raises 100 liters by approximately 0.5 ppm. Preferably the nitrate to phosphate ratio is maintained at a ratio of about 100:1 nitrate to phosphate. In one embodiment of the invention, nitrate is supplemented when the nitrate to phosphate ratio is less than about 75:1. In embodiments of the invention, the nitrogen source can be, nitrate compounds, urea compounds, ammonium compounds, nitric acid, or any water soluble nitrogen source that is biocompatible with animal inhabitants of the aquarium or aquaculture system. Nitrate and phosphate levels in the main tank can be measured by any appropriate means including titration, colorimeter analysis or spectrophotometric analysis.

In one aspect of the invention, iron and manganese are supplemented daily by adding about 1 drop to about 20 drops per 25 gallons of water in the system of a 10:1 iron and manganese solution with concentrations of 4 g/l of elemental iron in the form of iron citrate and 0.4 g/l manganese in the form of manganese citrate (1 drop is approximately 50 µl. In a preferred embodiment, 1 drop of the 10:1 iron to manganese solution is added daily per 25 gallons of water in the system. One drop contributes approximately 0.0002 g of iron and 0.00002 g of manganese. Amounts of 1 ml of a 20 g/l iron (in the form of iron citrate) and 0.2 g/l manganese (in the form of manganese citrate) per 10 gallons of water in the system can be used without adverse effects. Supplementation of the iron citrate and manganese citrate solution should be adjusted by observing the color and growth of the macroalgae in the bioreactor. When using *Chaetomorpha macroalgae*, for example, if the macroalgae is light green in color, additional supplementation is necessary and dark green color indicates sufficient supplementation.

Potassium, boron, and silica are added to the main tank as needed to maintain the growth of the macroalgae. Dosages are determined by test results. Boron is supplemented as needed to achieve about 4 ppm to less than about 20 ppm boron. Boron levels of about 4 ppm to about 6 ppm are preferred for reef aquariums. Boron levels in the main tank can be measured using titration tests (seawater is typically about 4.45 mg/l). Periodic macroalgae harvesting that occurs through the use of the bioreactors of the present invention exports a significant amount of boron out of the system water. When using *Chaetomorpha macroalgae*, a boron deficiency causes the *Chaetomorpha* to become brittle, which indicates additional boron supplementation is necessary. Boron level can be increased with a sodium tetraborate solution containing 1.739 grams sodium tetraborate per cup of fresh water, which raises 100 gallons of water about 1 ppm.

Potassium chloride solution is used as needed to supplement depleted levels of potassium. Natural levels of potassium is about 392 g/l at 35 ppt salinity. Silica is added as needed by adding sodium silicate solution. Natural levels of silica are about 2.9 g/l at 35 ppt salinity. Target levels are about 400 to about 425 g/l (K) and about 3 to about 6 g/l (Si). In addition, a lack of diatoms on the tank glass or other surfaces may indicate a need for added silica. If, however, diatoms are repopulating the tank glass or other surfaces in 24 hours, silica dosing is typically not necessary.

In one embodiment of the methods of the present invention, a strategy for altering the ratios of elements in the aquarium or aquaculture system for the purpose of limiting a specific element (or elements) in the system is by reference to Mulder's Chart. For example, to set phosphate as the limiting element in the system, nutrient levels in the system are measured. The nutrients are supplemented as described herein to achieve appropriate levels of elements and a nitrate to phosphate ratio above about 20:1 (16:1 and lower is generally considered nitrogen limited). If, however, the macroalgae growth rate is low despite, for example, testable levels of nitrogen, phosphate, magnesium, manganese, boron and iron being in desirable ranges and appropriate pH, salinity, and temperature, reference to Mulder's Chart indicates that a potential cause is low molybdenum concentration, preventing nitrogen uptake. Molybdenum could then be dosed at a conservative level as sodium molybdenate while observing growth results. A sample of system water could also be analyzed (by sending to a lab) for confirmation of low molybdenum levels before dosing.

Methods of Use

The present invention includes methods of maintaining the nutrient balance in an aquarium or aquaculture system comprising the steps: (i) providing a bioreactor of the present invention comprising macroalgae; (ii) supplementing nutrients; (iii) providing light; and (iv) periodically removing (harvesting) a portion of the macroalgae.

In one embodiment, the light source in the bioreactor is operated in a dark/light cycle with greater than or equal to about 8 hours of dark and greater than or equal to about 12 hours of light. In a preferred embodiment, the dark/light cycle in the bioreactor of the present invention is about 8 hours of dark and about 16 hours of light. In one embodiment, the dark/light cycle of the bioreactor is substantially reversed in comparison to the dark/light cycle of the main tank. For example, when the main tank is in a dark cycle, the bioreactor is substantially in a light cycle, and when the main tank is in a light cycle, the bioreactor is substantially in a dark cycle. In one embodiment, the light source for the bioreactor of the present invention is turned on about an hour before the tank lights and remains on for about an hour after the tank light turn off. Depending on the dark/light schedule of the main tank, the dark/light cycle of the bioreactor may not be perfectly reversed with respect to the main tank. For example, the light cycle of the bioreactor may overlap for a period of time with the light cycle of the main tank. Substantially reversing the dark/light cycle of the bioreactor with respect to the main tank helps prevent daily swings in pH and maintains stable dissolved oxygen levels throughout the dark cycle in the main tank. In a non photosynthetic culture system the dark/light cycles can be shortened so that up to 3 dark/light cycles occur in a 24 hour period (e.g., 5 hrs light/3 hrs dark), thereby reducing the pH swing that can occur with the bioreactors of the present invention operating on fish only systems.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references mentioned herein are incorporated in their entirety by reference into this application.

EXAMPLES

Example 1

A bioreactor as described in FIGS. 1-4 was assembled with small portions of *Chaetomorpha macroalgae* placed on each diffuser plate (and wrapped around the light tube) prior to inserting the armature assembly into the chamber assembly. The lid was closed and the hoses that carry water from the main tank and effluent from the bioreactor back to the main tank were connected. Water flow through the bioreactor was maintained at a rate of about 300 gph.

The light cycle of the bioreactor was controlled by a light timer with relay and programmed to operate with 16 hours of light and 8 hours of dark. The light phase of the bioreactor was set reverse to the tank lighting (reverse daylight cycle) to control daily pH swings.

Nutrient levels were monitored and supplemented with the purpose of making phosphate the limiting element for macroalgae growth. A 5% (w/v) solution of ammonium nitrate was dosed periodically to maintain about a 75:1 ratio of nitrate to phosphate. Silica levels were monitored and maintained by dosing with 130 g/l sodium silicate ($SiO_2$) where 10 ml raises 100 gallons of system water about 1 ppm $SiO_2$. Boron was also dosed regularly because salt mixes often lack adequate boron levels and demand from the growing macroalgae can be high. Boron levels were maintained by dosing with a sodium tetraborate solution (1.739 grams sodium tetraborate per cup of fresh water), which raises 100 gallons of tank water 1 ppm.

Example 2

Periodic maintenance was required to facilitate optimal growth of the macroalgae and proper nutrient balance in the main tank. Routine harvesting of the macroalgae was performed by turning off the feed pump and light source and disconnecting the effluent connector located at the top of the unit (allowing water in the unit to drain down). The armature and lighting assemblies were removed (together) from the chamber assembly and the *Chaetomorpha macroalgae* was emptied into a 5 gallon bucket. Tank water was added to the bucket to submerge the macroalgae, which was rinsed in the bucked to dislodge any bio-film growing on the macroalgae surface. The water from the bucket and up to about a third of the macroalgae was discarded. The remaining macroalgae was divided, stretched, and placed back onto each of the diffuser plates by wrapping the macroalgae around the light tube. The armature assembly (with the light assembly attached) was placed back into, and fastened to, the chamber assembly. The effluent line was reconnected to the bioreactor, the pump was turned back on, and standard operation of the unit was resumed as described in Example 1. For the first 20 days that the bioreactor was connected to the main tank, the rinsing and harvesting procedure was performed about every 4 to 5 days. Once the phosphate levels in the aquarium system were reduced through bioremediation by the macroalgae, the rinsing and harvesting procedure for the macroalgae was performed about every 10 to 14 days.

The invention claimed is:

1. A bioreactor for the bio-absorption of nutrients in an aquarium or aquaculture system comprising a light assembly, comprising an LED light source, that is mounted in an armature assembly comprising a light-transmissible tube and support structures for the growth of macroalgae, wherein the armature assembly is mounted within an outer chamber assembly, and wherein the light transmissible tube and the outer chamber define a growth chamber for the macroalgae.

2. The bioreactor of claim 1, wherein the growth chamber is substantially sealed from the surrounding atmosphere when the bioreactor is in use.

3. The bioreactor of claim 1, wherein the light assembly is removably mounted to the armature assembly and the armature assembly is removably mounted to the outer chamber assembly.

4. The bioreactor of claim 1, wherein the LED light source comprises a plurality of LED lights.

5. The bioreactor of claim 1, wherein the light assembly further comprises a cooling system.

6. The bioreactor of claim 5, wherein the cooling system comprises one or more of the group consisting of a water-based cooling system, a refrigerant-based cooling system, a conductive metal rod, and a heat pipe.

7. The bioreactor of claim 6, wherein the cooling system comprises a heat pipe.

8. The bioreactor of claim 6, wherein the cooling system comprises a water-based cooling system.

9. The bioreactor of claim 1 wherein the armature assembly comprises a lid removably affixed to the light tube, wherein the lid creates a substantially airtight and water tight seal with the chamber assembly when the device is assembled and in use.

10. The bioreactor of claim 9 wherein the lid of the armature assembly comprises an effluent port where water leaves the bioreactor to return to the main tank.

11. The bioreactor of claim 1, wherein the one or more support structures of the armature assembly are selected from the group consisting of baffle plates, axially radiating pins, axially radiating blades, and/or flexible coils or combinations thereof.

12. The bioreactor of claim 1, wherein the one or more support structures of the armature assembly comprise baffle plates movably affixed to the light tube.

* * * * *